US 6,689,572 B1

(12) United States Patent
Huang et al.

(10) Patent No.: US 6,689,572 B1
(45) Date of Patent: Feb. 10, 2004

(54) E. COLI AGGLUTINATION ASSAY

(75) Inventors: Ya Hei Huang, Taipei (TW);
Hsien-Chang Chang, Taipei (TW);
Tsung Chain Chang, Taipei (TW)

(73) Assignee: Executive Yuan, Council of Agriculture, Taipei (TW)

( * ) Notice: Subject to any disclaimer, the term of this patent is extended or adjusted under 35 U.S.C. 154(b) by 248 days.

(21) Appl. No.: 09/687,626

(22) Filed: Oct. 13, 2000

(51) Int. Cl.$^7$ .................... G01N 33/569; G01N 33/554; G01N 33/53; G01N 33/546
(52) U.S. Cl. .................. 435/7.37; 435/975; 435/7.1; 435/7.32; 435/7.3; 436/547; 436/533; 436/544
(58) Field of Search ............................ 435/7.32, 849, 435/7.37, 7.1, 7.3, 180, 975; 436/534, 528, 543, 535, 547, 544; 530/388.4, 825, 389.5, 391.1, 806

(56) References Cited

U.S. PATENT DOCUMENTS

| | | | | |
|---|---|---|---|---|
| 4,520,072 A | * | 5/1985 | Yoshino et al. | 428/403 |
| 5,418,140 A | | 5/1995 | Chang et al. | 435/7.32 |
| 5,536,644 A | | 7/1996 | Ullman et al. | 435/7.25 |
| 6,096,563 A | * | 8/2000 | Hajizadeh et al. | 436/523 |
| 6,235,494 B1 | * | 5/2001 | Hugli | 435/24 |
| 6,391,652 B2 | * | 5/2002 | Okada et al. | 436/518 |

FOREIGN PATENT DOCUMENTS

| | | |
|---|---|---|
| WO | 98 05687 A | 2/1998 |
| WO | 98 55871 A | 12/1998 |

OTHER PUBLICATIONS de Graaf et al. Infect. Immun. 36: 751–758, 1982, abstract.*
Vasquez et al. Vet. Microbiol. 48: 231–241, Feb. 1996, abstract.*
Faris et al. Zentralbl. Bakteriol. Mikrobiol. Hyg (A) 259 (4): 477–484, 1985.*
Wolf et al. Infect. Immun. 57 (1): 164–173, 1989, abstract.*
McConnell et al. FEMS Microbiol. Lett. 52 (1–2): 105–108, 1989, abstract.*
Thorns et al. Vet. Record 125: 91–92, 1989.*
Rice et al. J. Clin. Microbiol. 30: 1315–1316, 1992.*
Bänffer et al., "Evaluation of a Commercial Latex . . . ," Eur. J. Clin. Microbiol. Infect. Dis., 12:633–636, 1993.
Benge, G.R., "Detection of Salmonella . . . ," Eur. J. Clin. Microbiol. Dis, 8(4):294–298, 1989.

Chang et al., "Development of a Latex . . . ," Journal of Food Protection, 57(1):31–36, 1994.
Chang et al., "Evaluation of a Latex . . . ," Journal of Food Protection, 56(9):759–762, 1993.
Chang et al., "Efficacy of a Latex . . . ," Journal of AOAC International, 79(3):661–669, 1996.
Huang et al., "Comparison of the . . . ," Journal of Food Protection, 60(1):6–9, 1997.
Kerr et al., "Diagnostic application of . . . ," Journal of Applied Bacteriology, 72:302–308, 1992.
Koga et al., "Isolation and Characterization . . . ," Journal of General Micrbiology, 129:3185–3196, 1983.
Labadie et al., "Selection of cell wall . . . ," Journal of Applied Bacteriology, 72:220–226, 1992.
Lim et al., "Detection of Group D . . . ," Journal of Clinical Microbiology, 25(7):1165–1168, 1987.
March et al., "Latex Agglutination Test . . . ," Journal of Clinical Microbiology, 27(7):1675–1677, 1989.
Sowers et al., "Evaluation of Commercial Latex . . . ," Journal of Clinical Microbiology, 34(5):1286–1289, 1996.
Zhang et al., Evaluation of a Recombinant . . . , Microbiol. Immunol., 42(6):423–428, 1998.
Boyer et al., "Lack of Clinical Usefulness of a Positive Latex . . . ," Sep. 1993, Pediatric Infectious Disease Journal, vol. 12, No. 9; 779–780.
Huang et al., "Development of a Latex Agglutination Test for Rapid . . . ,", Feb. 2001, Eur.J.Clin.Microbiol.Infect.Dis., vol. 20, No. 2; 97–103.
Whitfield et al., "Biosynthesis and Assembly of the Polysialic Acid . . . ", 1984, J.Biol.Chem., vol. 259, No. 20;12776–12780.
York et al., "Multilaboratory Validation of Rapid Spotfor . . . ", J.Clin.Microbio., vol. 38, No. 9; 3394–3398.

* cited by examiner

Primary Examiner—S. Devi
(74) Attorney, Agent, or Firm—Fish & Richardson P.C.

(57) ABSTRACT

A method for detecting *Escherichia coli* in a sample by providing a sample suspected of containing *Escherichia coli*; contacting the sample with beads coated with a mixture of antibodies or anti-serum specific to one or more surface antigens of *Escherichia coli*, each of the one or more surface antigens having a molecular weight of 21±2 KDa, 26±2 KDa, 31±2 KDa, 36±2 KDa, 38±2 KDa, 67±2 KDa, or 77.8±2 KDa; and observing agglutination of the beads, where the presence of the agglutination indicates the presence of *Escherichia coli* in the sample.

12 Claims, No Drawings

E. COLI AGGLUTINATION ASSAY

BACKGROUND OF THE INVENTION

Although *Escherichia coli* is considered part of the normal bowel flora of healthy individuals, the microorganism is also recognized as an important pathogen in human diseases and conditions, including urinary tract infections, meningitis, and diarrhea. Therefore, a highly sensitive and specific method that can rapidly identify *E. coli* in biological samples would be useful.

SUMMARY OF THE INVENTION

The invention is based on the discovery that a highly sensitive and specific *E. coli* agglutination assay can be performed using antibodies against total urea-extracted *E. coli* antigens. Surprisingly, the sensitivity of the assay is dramatically reduced when using antibodies against specific *E. coli* antigens, even though such a strategy proved useful in agglutination assays for other bacterium (see, e.g., U.S. Pat. No. 5,418,140). Consequently, the invention relates in part to the unexpectedly superior performance of the assay using antibodies against total urea-extracted antigens, rather than specific surface antigens.

Accordingly, the invention features a method for detecting *Escherichia coli* in a sample by providing a sample suspected of containing *Escherichia coli*; contacting the sample with beads coated with a mixture of antibodies or anti-serum specific to one or more surface antigens of *Escherichia coli*, each of the one or more surface antigens having a molecular weight of 21±2 KDa, 26±2 KDa, 31±2 KDa, 36±2 KDa, 38±2 KDa, 67±2 KDa, or 77.8±2 KDa; and observing agglutination of the beads, where the presence of the agglutination indicates the presence of *Escherichia coli* in the sample. The method can further include determining whether a microorganism in the sample produces indole or ferments lactose, both of which are characteristic of *E. coli*.

The invention further features a kit for testing whether *E. coli* is present in a sample. The kit contains beads and a mixture of antibodies or antisera specific to one or more surface antigens of *Escherichic coli*, wherein each of the one or more surface antigens has a molecular weight selected from the group consisting of 21±2 KDa, 26±2 KDa, 31±2 KDa, 36±2 KDa, 38±2 KDa, 67±2 KDa, and 77.8±2 KDa. The kit can also include (1) a composition containing eosin-methylene blue for determining whether a microorganism ferments lactose, (2) a composition containing p-dimethylaminocinnamaldehyde for determining whether a microorganism produces indole, (3) a positive control reagent that is expected to agglutinate the beads coated with the mixture of antibodies, or (4) a negative control reagent that is not expected to agglutinate the beads coated with the mixture of antibodies.

As used herein, "total urea-extracted *Escherichia coli* antigens" means the antigens collected from the supernatant of a centrifuged mixture containing *E. coli* bacteria incubated in an aqueous mixture containing about 4 M urea.

Other features or advantages of the present invention will be apparent from the following detailed description, and also from the claims.

DETAILED DESCRIPTION

The invention relates to methods of detecting *E. coli* in a sample, such as a biological sample (e.g., a serum or cerebral spinal fluid sample) using an agglutination assay. While agglutination assays have been used to detect various species of bacteria in samples, the moieties attached to the beads and useful for agglutination are different, depending on the species to be detected (see, e.g., Chang et al., J. Food Protect. 57:31–36, 1994; and Chang et al., J. Food Protect. 56:759–762, 1993). Indeed, it is thus far uncertain which moieties are needed to detect a different species of bacterium.

The present invention is based in part on the identification of the particular moiety required for a highly sensitive and specific agglutination assay for detection of *E. coli*. As shown in the example below, the *E. coli* agglutination assay is not specific enough for clinical applications unless the beads are coated (e.g., by standard covalent or non-covalent methods) with a mixture of antibodies specific for total urea-extracted *E. coli* antigens. Such a mixture of antibodies can be produced by immunizing a vertebrate with total urea-extracted *E. coli* antigens and harvesting the antibodies produced by the animal, using standard techniques such as the ones described in the example below.

Without further elaboration, it is believed that one skilled in the art can, based on the above disclosure and the agglutination assays described below, utilize the present invention to its fullest extent. The following example is to be construed as merely illustrative of how one skilled in the art can isolate total urea-extracted *E. coli* antigens, immunize an animal with such antigens, and harvest antibodies produced by the animal, and are not limitative of the remainder of the disclosure in any way. Any publications cited in this disclosure are hereby incorporated by reference.

EXAMPLE

Materials and Methods

Bacterial strains and culture conditions. The microorganisms used in this study are listed in Table 1. A total of 1838 strains of gram-negative bacteria was tested, including 1028 strains of *E. coli* (among them, 748 strains were from clinical specimens, 268 strains from food samples, and 12 strains from the Culture Collection and Research Center [CCRC], Hsinchu, Taiwan), 632 strains of Enterobacteriaceae other than *E. coli*, 21 strains of Aeromonas spp., 75 strains of Pseudomonas spp., 18 strains of Vibrio spp, and 64 strains of other bacteria. Most strains were clinical isolates. All bacteria were first subcultured on tryptic soy agar (except *Vibrio parahaemolyticus*, was cultured on tryptic soy agar—2% NaCl), then subcultured on sheep blood agar and Levin's eosin-methylene blue (EMB) agar. The plates were incubated at 35° C. for 18 to 24 hours. Strains grown on EMB were observed for their ability to ferment lactose: strains having colonies of a brown (or black) center or metallic sheen were considered lactose fermenters. Bacteria grown on blood agar were tested for indole production by the spot indole test using the p-dimethylaminocinnarnaldehyde reagent (BBL DMACA Indole Reagent Droppers, Becton Dickinson Microbiology Systems, Cockeysville, Md.). Bacteria grown on blood agar were also used for the latex agglutination test (LAT).

Preparation of cell surface antigens. *E. coli* CCRC 15481 were grown on tryptic soy agar at 35° C. for 18 to 24 hours. The cells on each plate were collected by suspending them in 2 ml of phosphate-buffered saline (PBS; 10 mM phosphate buffer, 0.14 M NaCl, pH 7.2), and pelleting by centrifugation (2,000×g, 15 minutes) at room temperature. The bacterial cells were washed with PBS, suspended in 1 ml of 4 M urea, and incubated in a 50° C. water bath for 90 minutes with occasional shaking. The cell suspension was centrifuged (10,000×g, 15 minutes) at room temperature to remove insoluble particles, and the supernatant was dialyzed against 0.2× strength of PBS to remove urea. Cell surface antigens of two arbitrarily selected species (*Enterobacter sakazakii* CCRC 1415 and *Klebsiella pneumoniae* 06048, a clinical isolate) were also extracted with 4 M urea as controls.

Preparation and purification of antibodies. The *E. coli* urea-extracted cell surface antigens (abut 1 mg/ml) were emulsified with an equal volume of incomplete Freund's adjuvant (Difco Laboratories, Detroit, Mich.). Two milliliters of the emulsified antigen was injected subcutaneously into four to six sites on the back of each New Zealand White rabbit. The animals were boosted four times at 4-week interval, using the same injection conditions as the initial inoculation. Ten days after the final injection, ear arterial blood was collected. Antibody titers in sera were determined by an enzyme-linked immunosorbent assay (ELISA) using urea-extracted cell surface antigens (10 µg/ml) as the capture moiety, which coated the wells of a microtiter plate (Nunc, Kamstrup, Denmark). About 0.1 ml of a serially 10-fold diluted antisera was added to each well. After standard washings, horseradish peroxidase-labeled goat anti-rabbit IgG (Sigma Chemical Co., St. Louis, Mo.) was added to each well.

The IgG fraction of the antisera was purified by diethylaminoethyl (DEAE) ion-exchange chromatography as described in Linn et al., Proc. Natl. Acad. Sci. USA 70:1865–1869, 1973. The IgG was further purified by affinity chromatography using the urea-extracted cell antigens of *E. coli* coupled to CNBr-activated Sepharose™ 4B gel (Amersham Pharmacia Biotech, Uppsala, Sweden) using the manufacturer's instructions. Specific antibodies were eluted from the affinity column (1.5×5 cm) with 0.1 M glycine-HCl buffer, pH 2.6, and thereafter were immediately neutralized with 1 M Tris-HCl buffer, pH 8.0.

Sensitization of latex. Latex particles were coated with antibodies by physical adsorption. One milliliter of a 10% (wt./vol.) latex suspension (diameter 1.09 µm, Japan Synthetic Rubber, Tokyo) was washed two times with deionized water and suspended in 20 ml of water. To the washed latex suspension, an equal volume of affinity-purified antibodies (70 µg/ml) was added. The suspension was incubated at room temperature for 1 hour on an end-over-end mixer, and then centrifuged (2,000×g, 15 min) to remove unbound antibodies. The antibody-coated latex was washed twice with 0.1% bovine serum albumin, and resuspended in 20 ml of 0.1% bovine serum albumin. Control latex was coated with preimmune serum IgG in the same manner. The final concentration of latex reagent was 0.5% (wt./vol.)

Latex agglutination test. On a microscope slide, two circles with a diameter of about 1.5 cm were marked with a wax pencil. By using a sterile toothpick, one to two colonies grown overnight on blood agar were transferred to each circle on the slide. One drop of control latex was added to one circle (control circle), and one drop of test latex (sensitized with antibodies) was added to the other circle (test circle). The contents were smeared with the toothpick and gently rocked back and forth for 1 to 2 minutes. A test was positive if agglutination was observed in the test circle, while no agglutination was found in the control circle. A test was negative if no agglutination was found in the test circle. A few strains produced results of autoagglutination, i.e., agglutination was found in both control and test circles. These strains were excluded for calculation of test performance and were not included in Table 1.

sensitivity and specificity. Sensitivity was defined as the number of strains of *e. coli* that gave positive results (true positives) divided by total number of bacterial strains tested. specificity was defined as the number of non-*E. coli* strains that gave negative results (true negatives) divided by total number of bacterial strains tested.

Immunoblotting. To determine the molecular weights of the urea-extracted cell surface antigens, the Western blotting technique described by Hu et al., J. Immunol. Methods 202:113–121, 1997 was used with the following modifications. The urea-extracted antigens were separated by sodium dodecylsulfate polyacrylamide gel electrophoresis (SDS-PAGE) and blotted onto nitrocellulose membranes (Hybond ECL™, Amersham Pharmacia Biotech). After blotting, the lane of protein molecular weight markers was cut out, stained with 0.1% amidoblack and then destained. The remaining part of the membrane was blocked overnight at 4° C. in blocking solution (5% non-fat dry milk and 1% Tween™ 20). After washing, the blot was incubated with affinity-purified antibodies (0.5 µg/ml) produced as described above, and then with horseradish peroxidase-labeled goat anti-rabbit IgG (Sigma Chemical Co., 1:1,500 dilution). After washing, the membrane was developed in substrate solution (30 mg of 4-chloro-1-naphthol and 30 µl of 30% $H_2O_2$ in 10 ml methanol) to reveal the antigens recognized by the primary antibodies.

Results

In the beginning of this study, four surface antigens with molecular masses ranging from 20 to 90 KDa were purified from the total urea-extracted antigen is of *E. coli* (CCRC 15481) by preparative SDS-PAGE. Each of the four antigens was used to raise antibodies in rabbits, and the purified antibodies against the individual antigen were used to prepare latex reagent for the identification of *E. coli*. However, using antibodies against any one of the four antigens resulted in a relatively poor LAT sensitivity of less than 70%. This was surprising, given that a similar LAT using specific *Vibrio parahaemolyticus* surface antigens resulted in specificities well above 90% (U.S. Pat. No. 5,418,140). Thus, the failure to apply to *E. coli* a LAT strategy previously known to be successful for another bacterium indicated that successful strategies differ for different pathogenic bacteria, and that success with one strategy for one bacterium does not lead to a reasonable expectation of success for using the same strategy for another bacterium. In view of this unexpected but revealing finding, other strategies were contemplated. It was found that antibodies raised against total urea-extracted *E. coli* antigens were necessary for a highly sensitive LAT.

Titers of antisera. After a series of five immunizations, the titers of antisera against the urea-extracted cell surface antigens of *E. coli* 15481 were $10^7$, as determined by ELISA.

Immunoblotting. The affinity-purified antibodies recognized, multiple surface antigen is of *E. coli* CCRC 15481. These antigens were estimated to have molecular masses of 77.8, 67, 38, 36, 31, 26, and 21 kDa. Because the polyclonal antibodies were raised against multiple antigens of *E. coli*, it may have been expected that cross-reactions with antigens from other species were unavoidable. For example, 26 and 21 kDa antigens purified from *Enterobacter sakazakii* and *Klebsiella pneumoniae* also cross-reacted with the antibodies against total urea-extracted *E. coli* antigens.

The fact that a high level of specificity was nevertheless achieved, as shown below, provided another unexpected result.

Latex agglutination test. The results of LAT, indole production, and lactose fermnentation of the 1838 bacterial strains are listed in Table 1. Of the 1028 isolates of E. coli tested, 1021 strains (99.3%) yielded positive reactions of LAT, 1011 strains (98.3%) were positive for indole production, and 986 strains (95.9%) were lactose fermenters. Bacteria causing false-positive LAT were mainly from some isolates of Citrobacter, Enterobacter, Klebsiella, Morganella, Proteus, Serratia, and Shiglella (Table 1).

TABLE 1

| Microorganism | Source | No. of strains tested | LAT (+) | LAT (−) | indole (+) | lactose (+) |
|---|---|---|---|---|---|---|
| E. coli | Clinical, food, and CCRC | 1028 | 1021 | 7 | 1011 | 986 |
| Acinetobacter baumannii | Clinical | 11 | 0 | 11 | 0 | 2 |
| Acinetobacter calcoaceticus | Clinical | 6 | 1 | 5 | 0 | 3 |
| Acinetobacter lwoffii | Clinical | 3 | 0 | 3 | 0 | 1 |
| Acinetobacter spp. | Clinical | 2 | 0 | 2 | 0 | 1 |
| Aeromonas caviae | Clinical | 2 | 0 | 2 | 1 | 0 |
| Aeromonas hydrophila | Clinical | 13 | 0 | 13 | 12 | 11 |
| Aeromonas sobria | Clinical | 6 | 1 | 5 | 6 | 1 |
| Alcaligenes faecalis | Clinical | 1 | 0 | 1 | 0 | 0 |
| Alcaligenes xylosoxidans | Clinical | 2 | 0 | 2 | 0 | 0 |
| Citrobacter amalonaticus | Clinical | 5 | 0 | 5 | 5 | 3 |
| Citrobacter diversus | Clinical | 23 | 2 | 21 | 19 | 4 |
| Citrobacter freundii | Clinical | 57 | 8 | 49 | 4 | 50 |
| Edwardsiella tarda | Clinical | 3 | 0 | 3 | 3 | 0 |
| Enterobacter aerogenes | Clinical | 17 | 0 | 17 | 0 | 13 |
| Enterobacter agglomerans | Clinical | 8 | 0 | 8 | 0 | 3 |
| Enterobacter cloacae | Clinical | 63 | 5 | 58 | 0 | 20 |
| Enterobacter sakazakii | Clinical | 2 | 0 | 2 | 0 | 2 |
| Enterobacter spp. | Clinical | 7 | 1 | 6 | 0 | 3 |
| Escherichia blattae | CCRC | 3 | 0 | 3 | 0 | 0 |
| Escherichia fergusonii | CCRC | 5 | 1 | 4 | 4 | 0 |
| Escherichia hermannii | CCRC | 2 | 0 | 2 | 2 | 1 |
| Escherichia vulneris | CCRC | 5 | 0 | 5 | 0 | 0 |
| Flavobacterium indolgenes | Clinical | 5 | 0 | 5 | 0 | 0 |
| Flavobacterium meningosepticum | Clinical | 7 | 0 | 7 | 0 | 1 |
| Flavobacterium spp. | Clinical | 3 | 0 | 3 | 0 | 0 |
| Klebsiella oxytoca | Clinical | 32 | 3 | 29 | 31 | 30 |
| Klebsiella ozaenae | Clinical | 11 | 1 | 10 | 1 | 4 |
| Klebsiella pneumoniae | Clinical | 91 | 9 | 82 | 0 | 83 |
| Kurthia spp. | Clinical | 1 | 0 | 1 | 0 | 0 |
| Moraxella spp. | Clinical | 2 | 0 | 2 | 0 | 0 |
| Morganella morganii | Clinical | 83 | 3 | 80 | 64 | 2 |
| Pasteurella sp. | Clinical | 1 | 0 | 1 | 1 | 1 |
| Plesiomonas shigelloides | Clinical | 2 | 0 | 2 | 2 | 0 |
| Proteus mirabilis | Clinical | 46 | 10 | 36 | 0 | 0 |
| Proteus vulgaris | Clinical | 14 | 0 | 14 | 12 | 1 |
| Providencia rettgeri | Clinical | 2 | 0 | 2 | 0 | 0 |
| Providencia spp. | Clinical | 2 | 0 | 2 | 0 | 0 |
| Pseudomonas aeruginosa | Clinical | 50 | 1 | 49 | 0 | 0 |
| Pseudomonas cepacia | Clinical | 3 | 0 | 3 | 1 | 0 |
| Pseudomonas pickettii | Clinical | 11 | 0 | 11 | 0 | 0 |
| Pseudomonas putida | Clinical | 2 | 0 | 2 | 0 | 0 |
| Pseudomonas putrefaciens | Clinical | 3 | 0 | 3 | 0 | 0 |
| Pseudomonas stutzeri | Clinical | 4 | 0 | 4 | 1 | 1 |
| Pseudomonas spp. | Clinical | 2 | 0 | 2 | 0 | 1 |
| Salmonella choleraesuis subsp. choleraesuis | CCRC | 21 | 1 | 21 | 0 | 0 |
| Salmonella choleraesuis subsp. houtenae | CCRC | 2 | 0 | 2 | 0 | 0 |
| Salmonella group B | Clinical | 52 | 3 | 49 | 0 | 0 |
| Salmonella group C1 | Clinical | 3 | 0 | 3 | 0 | 0 |
| Salmonella group C2 | Clinical | 2 | 0 | 2 | 0 | 0 |
| Salmonella group D | Clinical | 15 | 1 | 5 | 0 | 0 |
| Serratia marcescens | Clinical | 23 | 4 | 19 | 0 | 1 |
| Serratia liquefaciens | Clinical | 1 | 0 | 1 | 0 | 0 |
| Shigella boydii | CCRC | 3 | 0 | 3 | 0 | 0 |
| Shigella flexneri | CCRC and Clinical | 8 | 4 | 4 | 0 | 0 |
| Shigella sonnei | CCRC and Clinical | 14 | 1 | 13 | 0 | 0 |
| Shigella spp. | Clinical | 4 | 1 | 3 | 0 | 0 |
| Sphingomonas paucimobilis | Clinical | 3 | 0 | 3 | 0 | 0 |
| Stenotrophomonas maltophilia | Clinical | 15 | 0 | 15 | 0 | 0 |

TABLE 1-continued

| Microorganism | Source | No. of strains tested | LAT (+) | LAT (−) | indole (+) | lactose (+) |
|---|---|---|---|---|---|---|
| Vibrio cholerae non-O1 | Clinical | 4 | 0 | 4 | 3 | 2 |
| Vibrio vulnificus | Clinical | 3 | 0 | 3 | 2 | 0 |
| Vibrio parahaemolyticus | Clinical | 11 | 0 | 11 | 11 | 0 |
| Yersinia enterocolitica | CCRC | 3 | 0 | 3 | 3 | 3 |

The sensitivities for the identification of E. coli based on the results of LAT, indole production, and lactose fermentation are shown in Table 2. Based on LAT only, the sensitivity was 99.3%. If LAT was used in conjunction with the indole production assay, lactose fermentation assay, or both assays, the sensitivities decreased to 98, 95.7, and 94.4%, respectively. About 5% of sensitivity was sacrificed by integrating LAT with the two additional biological assays for the identification of E. coli.

producing relatively low specificities were Shiglella (79.3%), Proteus (83.3%), Serratia (83.3%), and Citrobacter (88.2%). The glucose noni-fermenting bacteria (e.g., Acinetobacter, Pseudomonas, and Stenotrophomonas maltophilia) and. cytochrome oxidase-positive bacteria (e.g:, Vibrio and Aeromonas) displayed low cross-reactivity with the latex reagent. The overall specificity of LAT for the

TABLE 2

| | | No. of strains which were positive for | | | Sensitivity (%) based on strains which were positive for | | |
|---|---|---|---|---|---|---|---|
| Microorganism | No. of strains tested | LAT | Indole | Lactose | LAT | LAT and Indole | LAT and Lactose | LAT, indole, and lactose |
| E. coli | 1028 | 1021 | 1011 | 986 | 99.3 | 98.0 | 95.7 | 94.4 |

The specificities for the identification of E. coli based on the results of LAT, indole production, and lactose fermentation are shown in Table 3. Based on LAT only, the specificities ranged from 79.3 to 100 %, depending on the particular non-E. coli strains used for comparison. Strains identification of E. Coli was 93.3% (Table 3). The overall specificities increased to 98.8, 98.7, and 99.7%, respectively, if the production of indole, fermentation of lactose, or both assays, were used in conjunction with LAT for the identification of E. coli.

TABLE 3

| | | No. of strains which were positive for | | | Sensitivity (%) based on strains which were positive for | | | |
|---|---|---|---|---|---|---|---|---|
| Microorganism | No. of strains tested | LAT | Indole | Lactose | LAT | LAT and indole | LAT and lactose | LAT, indole, and lactose |
| Acinetobacter spp. | 22 | 1 | 0 | 7 | 95.5 | 100 | 95.5 | 100 |
| Aeromonas spp. | 21 | 1 | 19 | 12 | 95.2 | 95.2 | 100 | 100 |
| Citrobacter spp. | 85 | 10 | 28 | 57 | 88.2 | 95.3 | 91.8 | 97.6 |
| Enterobacter spp. | 97 | 6 | 0 | 41 | 93.8 | 100 | 100 | 100 |
| Escherichia spp.[b] | 15 | 1 | 6 | 1 | 93.3 | 93.3 | 100 | 100 |
| Flavobacterium spp. | 15 | 0 | 0 | 1 | 100 | 100 | 100 | 100 |
| Klebsiella spp. | 134 | 13 | 32 | 117 | 90.5 | 97.8 | 91.8 | 97.8 |
| Morganella morganii | 83 | 3 | 64 | 2 | 96.4 | 98.8 | 100 | 100 |
| Proteus spp. | 60 | 10 | 12 | 1 | 83.3 | 100 | 100 | 100 |
| Pseudomonas spp. | 75 | 1 | 2 | 2 | 98.7 | 100 | 100 | 100 |
| Salmonella spp. | 95 | 5 | 0 | 0 | 94.7 | 100 | 100 | 100 |
| Serratia spp. | 24 | 4 | 0 | 1 | 83.3 | 100 | 100 | 100 |
| Shigella spp. | 29 | 6 | 0 | 0 | 79.3 | 100 | 100 | 100 |
| Stenotrophomonas maltophilia | 15 | 0 | 0 | 0 | 100 | 100 | 100 | 100 |
| Vibrio spp. | 18 | 0 | 16 | 2 | 100 | 100 | 100 | 100 |
| Other bacteria[a] | 18 | 0 | | | 100 | 100 | 100 | 100 |
| Total | | | | | 93.3 | 98.8 | 98.7 | 99.7 |

[a]Including the following bacteria (number of strains): Alcaligenes spp. (3), Edwardsiella tarda (3), Kurthia sp. (1), Pasteurella spp. (1), Moroxella spp. (2), Plesiomonas shigelloides (2), Shingomonas paucimobilis (3), and Yersinia enterocolitica (3).
[b]Non-E. coli species.

Strains displaying both LAT- and indole-positive reactions included *Escherichia fergusonii, Morganella morganii* and a few isolates from Citrobacter and Klebsiella (Tables 1 and 3). Strains producing both LAT- and lactose-positive reactions were *Acinetobacter calcoaceticus, Morganella morganii* and a few isolates from Citrobacter and Klebsiella (Tables 1 and 3). In this study, 10% (3/30) of the strains of *Klebsiella oxytoca*, 3.5% (2/57) of the strains of *Citrobacter freundii*, and 4.3% (1/23) of the strains of *Citrobacter diversus* were LAT-, indole-, and lactose-positive.

In conclusion, suspect gram-negative *E. coli* bacilli can be accurately identified using agglutination with an overall sensitivity and specificity of 94.4 and 99.7%, respectively.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of this invention.

What is claimed is:

1. A kit for testing whether *Escherichia coli* is present in a sample, the kit comprising beads and a mixture of antibodies or anti-serum specific to a group of protein surface antigens of *Escherichiea coli*, wherein the group of antigens includes (1) a first antigen having a molecular weight of 21 KDa, (2) a second antigen having a molecular weight of 26 KDa, (3) a third antigen having a molecular weight of 31 KDa, (4) a fourth antigen having a molecular weight of 36 KDa, (5) a fifth antigen having a molecular weight of 38 KDa, (6) a sixth antigen having a molecular weight of 67 KDa, and (7) a seventh antigen having a molecular weight of 77.8 KDa, wherein the molecular weight is measured by SDS-PAGE.

2. The kit of claim 1, wherein the beads comprise latex.

3. The kit of claim 2, further comprising a composition comprising eosin-methylene blue.

4. The kit of claim 2, further comprising a composition comprising p-dimethylaminocinnamaldehyde.

5. The kit of claim 2, further comprising a positive control reagent that is expected to agglutinate beads coated with the mixture of antibodies or the anti-serum.

6. The kit of claim 2, further comprising a negative control reagent that is not expected to agglutinate beads coated with the mixture of antibodies or the anti-serum.

7. The kit of claim 1, further comprising a positive control reagent that is expected to agglutinate beads coated with the mixture of antibodies or the anti-serum.

8. The kit of claim 7, further comprising a negative control reagent that is not expected to agglutinate the beads coated with the mixture of antibodies or the anti-serum.

9. The kit of claim 1, further comprising a negative control reagent that is not expected to agglutinate beads coated with the mixture of antibodies or the anti-serum.

10. The kit of claim 1, further comprising a composition comprising eosin-methylene blue.

11. The kit of claim 10, further comprising a composition comprising p-dimethylaminocinnamaldehyde.

12. The kit of claim 1, further comprising a composition comprising p-dimethylaminocinnamaldehyde.

* * * * *